United States Patent
Isobe et al.

(10) Patent No.: US 10,858,678 B2
(45) Date of Patent: Dec. 8, 2020

(54) METHOD FOR PRODUCING 3-OXOADIPIC ACID

(71) Applicant: TORAY INDUSTRIES, INC., Tokyo (JP)

(72) Inventors: Kyohei Isobe, Kamakura (JP); Kenji Kawamura, Kamakura (JP); Masateru Ito, Kamakura (JP); Katsushige Yamada, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 149 days.

(21) Appl. No.: 16/060,182

(22) PCT Filed: Dec. 9, 2016

(86) PCT No.: PCT/JP2016/086668
§ 371 (c)(1),
(2) Date: Jun. 7, 2018

(87) PCT Pub. No.: WO2017/099209
PCT Pub. Date: Jun. 15, 2017

(65) Prior Publication Data
US 2018/0355385 A1     Dec. 13, 2018

(30) Foreign Application Priority Data
Dec. 11, 2015   (JP) .................................. 2015-241996

(51) Int. Cl.
  *C12P 7/50*    (2006.01)
  *C12R 1/01*    (2006.01)
  *C12R 1/645*   (2006.01)
  *C07C 51/44*   (2006.01)

(52) U.S. Cl.
CPC ............... *C12P 7/50* (2013.01); *C07C 51/44* (2013.01); *C12R 1/01* (2013.01); *C12R 1/645* (2013.01)

(58) Field of Classification Search
CPC ... C12P 7/50; C12R 1/645; C12R 1/01; C07C 51/44
See application file for complete search history.

(56) References Cited

FOREIGN PATENT DOCUMENTS

| | | |
|---|---|---|
| EP | 3498852 A1 | 6/2019 |
| JP | 51-28710 | 8/1976 |
| JP | 2012-59 A | 1/2012 |
| WO | WO 2009/151728 A2 | 12/2009 |

OTHER PUBLICATIONS

English translation of International Preliminary Report on Patentability and Written Opinion dated Jun. 12, 2018, in PCT/JP2016/086668.
English translation of International Search Report dated Mar. 7, 2017, in PCT/JP2016/086668.
Harwood, C. S. and R. E. Parales, "The β-ketoadipate Pathway and the Biology of Self-Identifying," Annu. Rev. Microbiol. (1996), vol. 50, pp. 553-590.
Nishimura et al., "Production of β-ketoadipate from lignin-derived substrates by engineering microbiological metabolism," Proceedings of the Annual Meeting of Japan Society for Bioscience, Biotechnology, and Agrochemistry (Mar. 5, 2012), vol. 2012, p. 3C23a04, with English translation.
Nishimura et al., "Production of novel biopolymer material from low-molecular-weight lignin using bacterial function," Proceedings of the Annual Meeting of Japan Society for Bioscience, Biotechnology, and Agrochemistry (Mar. 5, 2011), vol. 2011, p. 3C29p19, with English translation.
Polen et al., "Toward biotechnological production of adipic acid and precursors from biorenewables," Journal of Biotechnology (2013), vol. 167, pp. 75-84.
Song, "Characterization of Aromatic Hydrocarbon Degrading Bacteria Isolated from Pine Litter," Kor. J. Microbiol. Biotechnol. (2009), vol. 37, No. 4, pp. 333-339.
Tadasa, "Degradation of Eugenol by a Microorganism," Agric. Biol. Chem. (1977), vol. 41, No. 6, pp. 925-929.
Chapman et al., "The Bacterial Metabolism of 2,4-Xylenol," Biochem. J., vol. 110, 1968, pp. 491-498.

(Continued)

*Primary Examiner* — Delia M Ramirez
(74) *Attorney, Agent, or Firm* — Birch, Stewart, Kolasch & Birch, LLP

(57) ABSTRACT

A method of producing 3-oxoadipic acid from an aliphatic compound easily utilizable by a microorganism, such as a saccharide, by utilization of a metabolic pathway of the microorganism is disclosed. The method of producing 3-oxoadipic acid includes the step of culturing at least one type of microorganism having a capacity to produce 3-oxoadipic acid, selected from the group consisting of, for example, microorganisms belonging to the genus *Serratia*, microorganisms belonging to the genus *Corynebacterium*, microorganisms belonging to the genus *Hafnia*, microorganisms belonging to the genus *Bacillus*, microorganisms belonging to the genus *Escherichia*, microorganisms belonging to the genus *Pseudomonas*, microorganisms belonging to the genus *Acinetobacter*, microorganisms belonging to the genus *Alcaligenes*, microorganisms belonging to the genus *Shimwellia*, microorganisms belonging to the genus *Planomicrobium*, microorganisms belonging to the genus *Nocardioides*, microorganisms belonging to the genus *Yarrowia*, microorganisms belonging to the genus *Cupriavidus*, microorganisms belonging to the genus *Rhodosporidium*, microorganisms belonging to the genus *Streptomyces*, and microorganisms belonging to the genus *Microbacterium*.

4 Claims, No Drawings

(56) References Cited

OTHER PUBLICATIONS

The Extended European Search Report for European Application No. 16873102.4, dated Jul. 9, 2019.

Haußmann et al., "Global proteome survey of protocatechuate- and glucose-grown Corynebacterium glutamicum reveals multiple physiological differences," Journal of Proteomics, vol. 75, 2012, pp. 2649-2659.

Kadiyala et al., "High affinity p-nitrophenol oxidation by Bacillus sphaericus JS905," FEMS Microbiology Letters, vol. 166, 1998, pp. 115-120.

Kilby, "Formation of β-Ketoadipic Acid by Bacterial Fission of Aromatic Rings," Biochemistry, vol. 49, 1951, pp. 671-674.

Luu et al., "Integration of chemotaxis, transport and catabolism in Pseudomonas putida and identification of the aromatic acid chemoreceptor PcaY," Molecular Microbiology, vol. 96, No. 1, 2015, pp. 134-147.

Okamura-Abe et al., "Beta-ketoadipic acid and muconolactone production from a lignin-related aromatic compound through the protocatechuate 3,4-metabolic pathway," Journal of Bioscience and Bioengineering, vol. 121, Dec. 23, 2015, pp. 652-658.

METHOD FOR PRODUCING 3-OXOADIPIC ACID

TECHNICAL FIELD

The present invention relates to a method of producing 3-oxoadipic acid using a microorganism.

BACKGROUND ART

3-Oxoadipic acid (another name, β-ketoadipic acid; IUPAC name: 3-oxohexanedioic acid) is a dicarboxylic acid having a carbon number of 6 and a molecular weight of 160.12. 3-Oxoadipic acid can be used as a polyester by polymerization with a polyol, or as a raw material for a polyamide by polymerization with a polyamine. By lactamizing 3-oxoadipic acid by addition of ammonia to its terminus, it can even be used solely as a raw material for a polyamide.

3-Oxoadipic acid is produced by microorganisms including soil bacteria and fungi in the process of enzymatic degradation of an aromatic compound such as catechol or protocatechuic acid into a compound having a lower carbon number. This degradation pathway is generally known as the β-ketoadipate pathway.

A report related to a production method of 3-oxoadipic acid using a microorganism discloses a method of fermentative production of 3-oxoadipic acid from an aromatic compound(s) vanillic acid and/or protocatechuic acid using *Pseudomonas putida* KT2440 whose capacity to degrade 3-oxoadipic acid is eliminated by gene disruption (Patent Document 1). There is also a report suggesting that 3-oxoadipic acid (3-oxoadipate) can be produced as an intermediate in an adipic acid biosynthetic pathway in the process of a method of producing adipic acid using succinyl-CoA and acetyl-CoA as starting materials using a non-naturally occurring microorganism (Patent Document 2, FIG. 3).

PRIOR ART DOCUMENTS

Patent Documents

[Patent Document 1] JP 2012-000059 A
[Patent Document 2] WO 2009/151728

SUMMARY OF THE INVENTION

Problems to be Solved by the Invention

Although Patent Document 1 discloses a method of fermentative production of 3-oxoadipic acid using as a raw material(s) vanillic acid and/or protocatechuic acid, which are aromatic compounds that may be produced by degradation of lignin, there is no disclosure on fermentative production of 3-oxoadipic acid using an aliphatic compound as a raw material. In general, lignin degradation products obtained by chemical degradation contain a variety of aromatic compounds. When 3-oxoadipic acid is produced using a lignin degradation product as a raw material, a large amount of components non-metabolizable by microorganisms remain in the culture besides vanillic acid and/or protocatechuic acid. Thus, separation of 3-oxoadipic acid is difficult, and the utilization efficiency of the raw material is low, which is problematic.

Patent Document 2 describes that, in a microorganism artificially modified such that adipic acid can be produced, 3-oxoadipic acid (3-oxoadipate) can be produced as an intermediate of adipic acid which is the compound of interest. However, whether or not production of 3-oxoadipic acid is actually possible using a metabolic pathway in the microorganism has not been confirmed, and therefore whether or not production of 3-oxoadipic acid is possible using succinyl-CoA and acetyl-CoA as starting materials according to the description in Patent Document 2 has been unclear.

In view of this, the present invention aims to provide a method of producing 3-oxoadipic acid from an aliphatic compound easily utilizable by a microorganism such as a saccharide, by utilization of a metabolic pathway in the microorganism.

Means for Solving the Problems

As a result of intensive study for solving the above problem, the present inventors discovered the existence of naturally occurring microorganisms capable of producing 3-oxoadipic acid from an aliphatic compound using a metabolic pathway, thereby reaching the present invention described below.

That is, the present invention provides the following (1) to (29).

(1) A method of producing 3-oxoadipic acid, the method comprising the step of culturing at least one type of microorganism having a capacity to produce 3-oxoadipic acid, selected from the group consisting of microorganisms belonging to the genus *Serratia*, microorganisms belonging to the genus *Corynebacterium*, microorganisms belonging to the genus *Hafnia*, microorganisms belonging to the genus *Bacillus*, microorganisms belonging to the genus *Escherichia*, microorganisms belonging to the genus *Pseudomonas*, microorganisms belonging to the genus *Acinetobacter*, microorganisms belonging to the genus *Alcaligenes*, microorganisms belonging to the genus *Shimwellia*, microorganisms belonging to the genus *Planomicrobium*, microorganisms belonging to the genus *Nocardioides*, microorganisms belonging to the genus *Yarrowia*, microorganisms belonging to the genus *Cupriavidus*, microorganisms belonging to the genus *Rhodosporidium*, microorganisms belonging to the genus *Streptomyces*, microorganisms belonging to the genus *Microbacterium*, microorganisms belonging to the genus *Planomicrobium*, microorganisms belonging to the genus *Rhodosporidium*, microorganisms belonging to the genus *Saccharomyces*, and microorganisms belonging to the genus *Yersinia*.

(2) The method according to (1), comprising the step of culturing at least one type of microorganism having a capacity to produce 3-oxoadipic acid, selected from the group consisting of microorganisms belonging to the genus *Serratia*, microorganisms belonging to the genus *Corynebacterium*, microorganisms belonging to the genus *Hafnia*, microorganisms belonging to the genus *Bacillus*, microorganisms belonging to the genus *Escherichia*, microorganisms belonging to the genus *Pseudomonas*, microorganisms belonging to the genus *Acinetobacter*, microorganisms belonging to the genus *Alcaligenes*, microorganisms belonging to the genus *Shimwellia*, microorganisms belonging to the genus *Planomicrobium*, microorganisms belonging to the genus *Nocardioides*, microorganisms belonging to the genus *Yarrowia*, microorganisms belonging to the genus *Cupriavidus*, microorganisms belonging to the genus *Rhodosporidium*, microorganisms belonging to the genus *Streptomyces*, microorganisms belonging to the genus *Planomicrobium*, and microorganisms belonging to the genus *Rhodosporidium*.

(3) The method according to (1) or (2), wherein the microorganism belonging to the genus *Serratia* is *Serratia plymuthica*, *Serratia grimesii*, *Serratia ficaria*, *Serratia fonticola*, *Serratia odorifera*, *Serratia entomophila*, or *Serratia nematodiphila*.
(4) The method according to (3), wherein the microorganism belonging to the genus *Serratia* is *Serratia plymuthica*, *Serratia grimesii*, or *Serratia ficaria*.
(5) The method according to (1) or (2), wherein the microorganism belonging to the genus *Corynebacterium* is *Corynebacterium glutamicum*, *Corynebacterium acetoacidophilum*, *Corynebacterium acetoglutamicum*, or *Corynebacterium ammoniagenes*.
(6) The method according to (1) or (2), wherein the microorganism belonging to the genus *Hafnia* is *Hafnia alvei*.
(7) The method according to (1) or (2), wherein the microorganism belonging to the genus *Bacillus* is *Bacillus badius*, or *Bacillus megaterium*.
(8) The method according to (1) or (2), wherein the microorganism belonging to the genus *Escherichia* is *Escherichia coli* or *Escherichia fergusonii*.
(9) The method according to (1) or (2), wherein the microorganism belonging to the genus *Pseudomonas* is *Pseudomonas putida*, *Pseudomonas fragi*, *Pseudomonas fluorescens*, *Pseudomonas reptilivora*, or *Pseudomonas azotoformans*.
(10) The method according to (1) or (2), wherein the microorganism belonging to the genus *Acinetobacter* is *Acinetobacter radioresistens*.
(11) The method according to (1) or (2), wherein the microorganism belonging to the genus *Alcaligenes* is *Alcaligenes faecalis*.
(12) The method according to (1) or (2), wherein the microorganism belonging to the genus *Shimwellia* is *Shimwellia Blattae*.
(13) The method according to (1) or (2), wherein the microorganism belonging to the genus *Planomicrobium* is *Planomicrobium okeanokoites*.
(14) The method according to (1) or (2), wherein the microorganism belonging to the genus *Nocardioides* is *Nocardioides albus*.
(15) The method according to (1) or (2), wherein the microorganism belonging to the genus *Yarrowia* is *Yarrowia lipolytica*.
(16) The method according to (1) or (2), wherein the microorganism belonging to the genus *Cupriavidus* is *Cupriavidus necator*.
(17) The method according to (1) or (2), wherein the microorganism belonging to the genus *Rhodosporidium* is *Rhodosporidium toruloides*.
(18) The method according to (1) or (2), wherein the microorganism belonging to the genus *Streptomyces* is *Streptomyces olivaceus*.
(19) The method according to (1), wherein the microorganism belonging to the genus *Microbacterium* is *Microbacterium ammoniaphilum*.
(20) The method according to (1) or (2), wherein the microorganism belonging to the genus *Planomicrobium* is *Planomicrobium okeanokoites*.
(21) The method according to (1) or (2), wherein the microorganism belonging to the genus *Rhodosporidium* is *Rhodosporidium toruloides*.
(22) The method according to (1), wherein the microorganism belonging to the genus *Saccharomyces* is *Saccharomyces cerevisiae*.
(23) The method according to (1), wherein the microorganism belonging to the genus *Yersinia* is *Yersinia ruckeri*.
(24) The method according to any one of (1) to (23), wherein the medium for culturing the microorganism contains an aliphatic compound.
(25) The method according to any one of (1) to (24), wherein the medium for culturing the microorganism contains an aliphatic compound utilizable as a sole carbon source for growth of the microorganism.
(26) The method according to any one of (1) to (25), wherein the medium for culturing the microorganism contains at least one carbon source selected from the group consisting of saccharides, succinic acid, 2-oxoglutaric acid, and glycerol.
(27) The method according to any one of (1) to (26), wherein the microorganism is cultured in a medium containing at least one inducer selected from the group consisting of ferulic acid and p-coumaric acid.

Effect of the Invention

By the present invention, 3-oxoadipic acid can be obtained using a metabolic pathway of a microorganism.

MODE FOR CARRYING OUT THE INVENTION

The method of producing 3-oxoadipic acid of the present invention comprises a step of culturing a microorganism having a capacity to produce 3-oxoadipic acid. More specifically, the present invention is characterized in that 3-oxoadipic acid is produced using a metabolic pathway of a microorganism having a capacity to produce 3-oxoadipic acid, by culturing the microorganism.

The microorganism having a capacity to produce 3-oxoadipic acid used in the method of the present invention is selected from the following microorganisms.
  Microorganisms belonging to the genus *Serratia*
  Microorganisms belonging to the genus *Corynebacterium*
  Microorganisms belonging to the genus *Pseudomonas*
  Microorganisms belonging to the genus *Bacillus*
  Microorganisms belonging to the genus *Hafnia*
  Microorganisms belonging to the genus *Escherichia*
  Microorganisms belonging to the genus *Acinetobacter*
  Microorganisms belonging to the genus *Alcaligenes*
  Microorganisms belonging to the genus *Shimwellia*
  Microorganisms belonging to the genus *Planomicrobium*
  Microorganisms belonging to the genus *Nocardioides*
  Microorganisms belonging to the genus *Yarrowia*
  Microorganisms belonging to the genus *Cupriavidus*
  Microorganisms belonging to the genus *Rhodosporidium*
  Microorganisms belonging to the genus *Streptomyces*
  Microorganisms belonging to the genus *Microbacterium*
  Microorganisms belonging to the genus *Planomicrobium*
  Microorganisms belonging to the genus *Rhodosporidium*
  Microorganisms belonging to the genus *Saccharomyces*
  Microorganisms belonging to the genus *Yersinia*

Specific examples of the microorganisms belonging to the genus *Serratia* having a capacity to produce 3-oxoadipic acid include *Serratia plymuthica*, *Serratia grimesii*, *Serratia ficaria*, *Serratia fonticola*, *Serratia odorifera*, *Serratia entomophila*, and *Serratia nematodiphila*. The mechanism by which microorganisms belonging to the genus *Serratia* can produce 3-oxoadipic acid using their metabolic pathway is not clear. Since, for example, microorganisms belonging to the genus *Serratia* are used for a wastewater processing method in which discharged excess sludge is reduced (see JP 2002-18469 A), it is assumed that they have a complex metabolic pathway which is different from those of microorganisms commonly used for matter production, and that they produce 3-oxoadipic acid based on this metabolic pathway.

Specific examples of the microorganisms belonging to the genus *Corynebacterium* having a capacity to produce 3-oxoadipic acid include *Corynebacterium glutamicum, Corynebacterium acetoacidophilum, Corynebacterium acetoglutamicum,* and *Corynebacterium ammoniagenes.* The mechanism by which microorganisms belonging to the genus *Corynebacterium* can produce 3-oxoadipic acid using their metabolic pathway is also not clear. Since, for example, microorganisms belonging to the genus *Corynebacterium* are used for a wastewater processing method in which discharged excess sludge is reduced (see JP 2002-18469 A), it is assumed that, although they are microorganisms commonly used for matter production, they also have a complex metabolic pathway which is different from metabolic pathways for the conventional matter production, and that they produce 3-oxoadipic acid based on this metabolic pathway.

Specific examples of the microorganisms belonging to the genus *Psuedomonas* having a capacity to produce 3-oxoadipic acid include *Pseudomonas putida, Pseudomonas fragi, Pseudomonas fluorescens, Pseudomonas reptilivora,* and *Pseudomonas azotoformans.* The mechanism by which microorganisms belonging to the genus *Psuedomonas* can produce 3-oxoadipic acid using their metabolic pathway is also not clear. Since, for example, microorganisms belonging to the genus *Psuedomonas* are known to degrade aromatic hydrocarbon solvents, petroleum hydrocarbon solvents, ester solvents, alcohol solvents, and the like (see JP 2010-130950 A), it is assumed that they have a complex metabolic pathway which is different from those of microorganisms commonly used for matter production, and that they produce 3-oxoadipic acid based on this metabolic pathway.

Specific examples of the microorganisms belonging to the genus *Bacillus* having a capacity to produce 3-oxoadipic acid include *Bacillus megaterium* and *Bacillus badius.* The mechanism by which microorganisms belonging to the genus *Bacillus* can produce 3-oxoadipic acid using their metabolic pathway is also not clear. Since, for example, microorganisms belonging to the genus *Bacillus* are used for deodorization of malodorous substances generated by fermentation of organic wastes (JP 2001-120945 A), it is assumed that, although they are microorganisms commonly used for matter production, they also have a complex metabolic pathway which is different from metabolic pathways for the conventional matter production, and that they produce 3-oxoadipic acid based on this metabolic pathway.

Specific examples of the microorganisms belonging to the genus *Hafnia* having a capacity to produce 3-oxoadipic acid include *Hafnia alvei.* The mechanism by which microorganisms belonging to the genus *Hafnia* can produce 3-oxoadipic acid using their metabolic pathway is also not clear. Since, for example, microorganisms belonging to the genus *Hafnia* are used for increasing the terephthalic acid degradation rate of microorganisms for degradation of terephthalic acid-containing waste liquids (see JP 10-52256 A), it is assumed that they have a complex metabolic pathway which is different from those of microorganisms commonly used for matter production, and that they produce 3-oxoadipic acid based on this metabolic pathway.

Specific examples of the microorganisms belonging to the genus *Escherichia* having a capacity to produce 3-oxoadipic acid include *Escherichia coli* and *Escherichia fergusonii.* The mechanism by which microorganisms belonging to the genus *Escherichia* can produce 3-oxoadipic acid using their metabolic pathway is also not clear. Since, for example, microorganisms belonging to the genus *Escherichia* are known to have a hydrocarbon degradation capacity and heavy-metal resistance (see Bioresource Technology, 2011, 102, 19, 9291-9295), it is assumed that, although they are microorganisms commonly used for matter production, they also have a complex metabolic pathway which is different from metabolic pathways for the conventional matter production, and that they produce 3-oxoadipic acid based on this metabolic pathway.

Specific examples of the microorganisms belonging to the genus *Acinetobacter* having a capacity to produce 3-oxoadipic acid include *Acinetobacter radioresistens.* The mechanism by which microorganisms belonging to the genus *Acinetobacter* can produce 3-oxoadipic acid using their metabolic pathway is also not clear. Since, for example, the genus *Acinetobacter* is known to degrade mineral oils such as benzene, fuel oils, and lubricating oils, and hence to be applicable to environmental cleanup (see JP 2013-123418 A), it is assumed that they have a complex metabolic pathway which is different from those of microorganisms commonly used for matter production, and that they produce 3-oxoadipic acid based on this metabolic pathway.

Specific examples of the microorganisms belonging to the genus *Alcaligenes* having a capacity to produce 3-oxoadipic acid include *Alcaligenes faecalis.* The mechanism by which microorganisms belonging to the genus *Alcaligenes* can produce 3-oxoadipic acid using their metabolic pathway is also not clear. Since, for example, the genus *Alcaligenes* is known to be applicable to degradation of polycyclic aromatic compounds such as pyrene (see JP 2003-70463 A), it is assumed that they have a complex metabolic pathway which is different from those of microorganisms commonly used for matter production, and that they produce 3-oxoadipic acid based on this metabolic pathway.

Specific examples of the microorganisms belonging to the genus *Shimwellia* having a capacity to produce 3-oxoadipic acid include *Shimwellia blattae.* The mechanism by which microorganisms belonging to the genus *Shimwellia* can produce 3-oxoadipic acid using their metabolic pathway is also not clear. Since, for example, the genus *Shimwellia* inhabits even places with high concentrations of radioactive radon (see Radiation Protection and Environment, 2014, 37, 1, 21-24), it is assumed that they have a complex metabolic pathway which is different from those of microorganisms commonly used for matter production, and that they produce 3-oxoadipic acid based on this metabolic pathway.

Specific examples of the microorganisms belonging to the genus *Planomicrobium* having a capacity to produce 3-oxoadipic acid include *Planomicrobium okeanokoites.* The mechanism by which microorganisms belonging to the genus *Planomicrobium* can produce 3-oxoadipic acid using their metabolic pathway is also not clear. Since, for example, the genus *Planomicrobium* is known to degrade diesel oils (see Journal of Basic Microbiology, Volume 53, Issue 9, pages 723-732), it is assumed that they have a complex metabolic pathway which is different from those of microorganisms commonly used for matter production, and that they produce 3-oxoadipic acid based on this metabolic pathway.

Specific examples of the microorganisms belonging to the genus *Nocardioides* having a capacity to produce 3-oxoadipic acid include *Nocardioides albus.* The mechanism by which microorganisms belonging to the genus *Nocardioides* can produce 3-oxoadipic acid using their metabolic pathway is also not clear. Since, for example, the genus *Nocardioides* is used for degradation of poorly degradable aromatic compounds (see JP 2003-250529 A), it is assumed that they have a complex metabolic pathway which is different from those of microorganisms commonly used for matter production, and that they produce 3-oxoadipic acid based on this metabolic pathway.

Specific examples of the microorganisms belonging to the genus *Yarrowia* having a capacity to produce 3-oxoadipic acid include *Yarrowia lipolytica*. The mechanism by which microorganisms belonging to the genus *Yarrowia* can produce 3-oxoadipic acid using their metabolic pathway is also not clear. Since, for example, the genus *Yarrowia* is used for degradation of fats/oils and fatty acids (JP 2015-192611 A), it is assumed that they have a complex metabolic pathway which is different from those of microorganisms commonly used for matter production, and that they produce 3-oxoadipic acid based on this metabolic pathway.

Specific examples of the microorganisms belonging to the genus *Cupriavidus* having a capacity to produce 3-oxoadipic acid include *Cupriavidus necator*. The mechanism by which microorganisms belonging to the genus *Capriavidus* can produce 3-oxoadipic acid using their metabolic pathway is not clear. Since, for example, the genus *Capriavidus* is known to degrade hydrocarbons derived from petroleum products such as benzene, toluene, and xylene (see JP 2007-252285 A), and to have metal tolerance (Antonie van Leeuwenhoek, 2009, 96, 2, 115-139), it is assumed that microorganisms belonging to the genus *Capriavidus* have a complex metabolic pathway which is different from those of microorganisms commonly used for matter production, and that they produce 3-oxoadipic acid based on this metabolic pathway.

Specific examples of the microorganisms belonging to the genus *Rhodosporidium* having a capacity to produce 3-oxoadipic acid include *Rhodosporidium toruloides*. The mechanism by which microorganisms belonging to the genus *Rhodosporidium* can produce 3-oxoadipic acid using their metabolic pathway is also not clear. Since, for example, the genus *Rhodosporidium* is known to degrade diesel oils (Research Journal of Environmental Toxicology 5 (6): 369-377, 2011), it is assumed that they have a complex metabolic pathway which is different from those of microorganisms commonly used for matter production, and that they produce 3-oxoadipic acid based on this metabolic pathway.

Specific examples of the microorganisms belonging to the genus *Streptomyces* having a capacity to produce 3-oxoadipic acid include *Streptomyces olivaceus*. The mechanism by which microorganisms belonging to the genus *Streptomyces* can produce 3-oxoadipic acid using their metabolic pathway is also not clear. Since, for example, the genus *Streptomyces* is used for degradation of polyhydroalkanoate resins (WO 05/045017), it is assumed that, although they are microorganisms commonly used for matter production, they also have a complex metabolic pathway which is different from metabolic pathways for the conventional matter production, and that they produce 3-oxoadipic acid based on this metabolic pathway.

Specific examples of the microorganisms belonging to the genus *Microbacterium* having a capacity to produce 3-oxoadipic acid include *Microbacterium ammoniaphilum*. The mechanism by which microorganisms belonging to the genus *Microbacterium* can produce 3-oxoadipic acid using their metabolic pathway is also not clear. Since the genus *Microbacterium* is used for a method of processing lignin-containing waste liquids (JP 2009-72162 A), it is assumed that they have a complex metabolic pathway which is different from those of microorganisms commonly used for matter production, and that they produce 3-oxoadipic acid based on this metabolic pathway.

Specific examples of the microorganisms belonging to the genus *Planomicrobium* having a capacity to produce 3-oxoadipic acid include *Planomicrobium okeanokoites*. The mechanism by which microorganisms belonging to the genus *Planomicrobium* can produce 3-oxoadipic acid using their metabolic pathway is also not clear. Since, for example, the genus *Planomicrobium* is used for biodegradation of benzene and derivatives thereof (Res Microbiol. 2006 September; 157(7): 629-36), it is assumed that they have a complex metabolic pathway which is different from those of microorganisms commonly used for matter production, and that they produce 3-oxoadipic acid based on this metabolic pathway.

Specific examples of the microorganisms belonging to the genus *Rhodosporidium* having a capacity to produce 3-oxoadipic acid include *Rhodosporidium toruloides*. The mechanism by which microorganisms belonging to the genus *Rhodosporidium* can produce 3-oxoadipic acid using their metabolic pathway is also not clear. Since, for example, the genus *Rhodosporidium* is used for biodegradation of diesel oils (Research Journal of Environmental Toxicology 5.6 (November/December 2011): 369-377), it is assumed that they have a complex metabolic pathway which is different from those of microorganisms commonly used for matter production, and that they produce 3-oxoadipic acid based on this metabolic pathway.

Specific examples of the microorganisms belonging to the genus *Saccharomyces* having a capacity to produce 3-oxoadipic acid include *Saccharomyces cerevisiae*. The mechanism by which microorganisms belonging to the genus *Saccharomyces* can produce 3-oxoadipic acid using their metabolic pathway is also not clear. Since, for example, the genus *Saccharomyces* degrades an azo dye methyl red (Chemosphere. 2007 June; 68(2): 394-400), it is assumed that, although they are microorganisms commonly used for matter production, they also have a complex metabolic pathway which is different from metabolic pathways for the conventional matter production, and that they produce 3-oxoadipic acid based on this metabolic pathway.

Specific examples of the microorganisms belonging to the genus *Yersinia* having a capacity to produce 3-oxoadipic acid include *Yersinia ruckeri*. The mechanism by which microorganisms belonging to the genus *Yersinia* can produce 3-oxoadipic acid using their metabolic pathway is also not clear. Since, for example, the genus *Yersinia* is involved in biodegradation of pesticides (Revista Internacional de Contaminacion Ambiental; Vol 26, No 1 (2010); 27-38), it is assumed that they have a complex metabolic pathway which is different from those of microorganisms commonly used for matter production, and that they produce 3-oxoadipic acid based on this metabolic pathway.

All of the microorganisms described above are known as microorganisms present in nature, and can be isolated from natural environments such as soils. They can also be purchased from microorganism-distributing agencies such as ATCC.

The microorganism may be one prepared by recombination of a gene(s) according to a known method, or one mutated by artificial mutation means, such that the productivity of 3-oxoadipic acid increases.

The fact that the microorganism has a capacity to produce 3-oxoadipic acid can be confirmed by subjecting the supernatant of the culture liquid to an appropriate analysis method such as high-performance liquid chromatography (HPLC), high-performance liquid chromatography-mass spectrometry (LC/MS), high-performance liquid chromatography-tandem mass spectrometry (LC-MS/MS), gas chromatography (GC), or gas chromatography-mass spectrometry (GC/MS), to detect 3-oxoadipic acid contained in the culture supernatant. In the present invention, it is preferred to use, as the microorganism having a capacity to produce 3-oxoadipic acid, a microorganism capable of producing not less than 1.0 mg/L of 3-oxoadipic acid into a culture supernatant obtained by culturing the microorganism for 20 hours.

In the present invention, the microorganism is cultured in a medium suitable for the microorganism used, for example, in a medium, preferably a liquid medium, containing an aliphatic compound that can be metabolized by ordinary microorganisms as a carbon source. Here, the "metabolism" in the present invention means that a certain chemical substance which is incorporated from the outside of the cell or generated from another chemical substance in the cell by a microorganism is converted to another chemical substance by enzymatic reaction. The medium to be used contains, besides the carbon source metabolizable by the microorganism used, suitable amounts of a nitrogen source, inorganic salt, and, if necessary, an organic micronutrient such as amino acid or vitamin. As long as the above nutrient sources are contained, the medium to be used may be either a natural medium or synthetic medium. Since the above microorganisms are known, and their culture methods as well as the media to be used therefor are also known, each microorganism can be cultured using a known medium and a known culture method.

Examples of the aliphatic compound metabolizable as a carbon source by the above microorganisms include saccharides such as glucose, sucrose, fructose, galactose, mannose, xylose, and arabinose; starch saccharified liquids, molasses, and cellulose-containing biomass saccharified liquids containing these saccharides; organic acids such as acetic acid, succinic acid, lactic acid, fumaric acid, citric acid, propionic acid, malic acid, and malonic acid; monovalent alcohols such as methanol, ethanol, and propanol; polyols such as glycerin, ethylene glycol, and propanediol; hydrocarbons; fatty acids; and fats/oils. The aliphatic compound may be any of the above compounds as long as it is metabolizable by the microorganism. The aliphatic compound is preferably one utilizable by the microorganism as a sole carbon source for its growth. Examples of such an aliphatic compound include glucose, xylose, glycerol, succinic acid, and acetic acid. More preferably, 3-oxoadipic acid can be efficiently produced by allowing metabolism of an organic acid(s) and a saccharide(s); an organic acid(s) and an alcohol(s); or two or more kinds of organic acids; in combination. In such cases, either one of the aliphatic compounds to be metabolized may be an aliphatic compound incorporated by the microorganism from the outside of the cell, or may be an aliphatic compound generated from another chemical substance in the cell. In such combinations, examples of the organic acid and the saccharide include succinic acid and glucose; and succinic acid and xylose. Examples of the organic acid and the alcohol include succinic acid and glycerol. Examples of the two or more kinds of organic acids include succinic acid and acetic acid. The concentration of the metabolizable aliphatic compound(s) is not limited as long as it is a concentration at which the microorganism to be cultured can be maintained, and a known concentration for each microorganism may be employed. Normally, the concentration in the whole medium is usually about 5 g/L to 300 g/L, especially about 10 g/L to 150 g/L (total concentration, in cases where two or more kinds of aliphatic compounds are contained).

Examples of the nitrogen source used for the culture of the microorganism include ammonia gas, aqueous ammonia, ammonium salts, urea, nitric acid salts, and other supplementary organic nitrogen sources, for example, oil cakes, soybean hydrolysates, casein digests, other amino acids, vitamins, corn steep liquor, yeasts or yeast extracts, meat extracts, peptides such as peptone, and various fermentation microorganism cells and hydrolysates thereof. The nitrogen sources may be used individually, or in combination of two or more thereof. It is also possible to use the combination of an inorganic nitrogen source(s) and an organic nitrogen source(s). The concentration of the nitrogen source(s) is not limited as long as it is a concentration at which the microorganism to be cultured can be maintained, and a known concentration for each microorganism may be employed. The concentration is usually about 0.1 g/L to 50 g/L, especially about 0.5 g/L to 10 g/L (total concentration, in cases where two or more kinds of nitrogen sources are contained).

Examples of inorganic salts which may be added as appropriate to be used for the culture of the microorganism include phosphoric acid salts, magnesium salts, calcium salts, iron salts, and manganese salts. The concentration of the inorganic salt is not limited as long as it is a concentration at which the microorganism to be cultured can be maintained, and a known concentration for each microorganism may be employed. The concentration of each inorganic salt is usually about 1 g/L to 50 g/L, especially about 5 g/L to 20 g/L.

Conditions for the culture of the microorganism to be set for the production of 3-oxoadipic acid, such as the medium having the component composition described above, culture temperature, stirring rate, pH, aeration rate, inoculation amount, and culture time, may be appropriately controlled or selected based on the type of the production microorganism used, external conditions, and/or the like. The culture temperature may be, for example, about 10° C. to 50° C., especially about 20° C. to 40° C.; the pH may be, for example, about 3 to 9, especially 5 to 7; and the culture time may be, for example, about 1 hour to 200 hours, especially about 24 hours to 150 hours; although the conditions are not limited to these. In cases where foaming occurs in the liquid culture, an antifoaming agent such a mineral oil, silicone oil, or surfactant may be included as appropriate in the medium.

By the medium and the culture conditions described above, 3-oxoadipic acid can be produced by culture using the above microorganism. More efficient production of 3-oxoadipic acid is possible by culturing the microorganism in a state where a metabolic pathway required for the production of 3-oxoadipic acid is activated. The method of activating the metabolic pathway is not limited, and examples of the method include a method in which an inducer(s) is/are added to the medium to induce expression of an enzyme gene(s) in a metabolic pathway(s) for production of 3-oxoadipic acid; a method in which a coding region(s) of an enzyme gene(s) and/or a functional region(s) in the vicinity thereof is/are modified by a gene modification technique; a method in which the copy number(s) of an enzyme gene(s) is/are increased; and a method in which an enzyme gene function(s) in a biosynthetic pathway(s) of a by-product(s) is/are destroyed. The method is preferably a method in which expression of an enzyme gene(s) in a metabolic pathway(s) for production of 3-oxoadipic acid is induced by an inducer(s).

The inducer used in the present invention is not limited as long as it is a substance that activates a metabolic pathway required for the production of 3-oxoadipic acid. Examples of inducers which may be usually used include aromatic compounds, and aliphatic compounds having a carbon number of not less than 6, which are metabolized into compounds having smaller carbon numbers through 3-oxoadipyl-CoA as an intermediate. The aliphatic compound having a carbon number of not less than 6 may be preferably a dicarboxylic acid having a carbon number of not less than 6. Examples of such a compound can be known using a database such as KEGG (Kyoto Encyclopedia of Genes and Genomes). Specific examples of the compound include benzoic acid, cis,cis-muconic acid, terephthalic acid, protocatechuic acid, catechol, vanillin, coumaric acid, ferulic acid, adipic acid, phenylalanine, and phenethylamine. Preferred examples of the compound include benzoic acid, catechol, protocatechuic acid, and adipic acid.

The above inducers may be used either individually or in combination of two or more thereof depending on the microorganism used for the production of 3-oxoadipic acid. The concentration of the inducer is not limited, and may be set appropriately. The concentration is usually about 1 mg/L to 10 g/L, especially about 3 mg/L to 1 g/L (total concentration, in cases where two or more kinds of inducers are used).

The 3-oxoadipic acid produced in the culture of the microorganism can be isolated according to a common method in which the culture is stopped at a time point when the accumulated amount reached an appropriate level, and then a fermentation product is collected from the culture. More specifically, for example, after separating microbial cells by centrifugation, filtration, and/or the like, 3-oxoadipic acid can be isolated from the culture by column chromatography, ion-exchange chromatography, activated carbon treatment, crystallization, membrane separation, distillation, and/or the like. Still more specifically, preferred examples of the recovering method include, but are not limited to, a method in which the culture is subjected to removal of water by a concentration operation using a reverse osmosis membrane, evaporator, and/or the like to increase the concentration of 3-oxoadipic acid, and crystals of 3-oxoadipic acid and/or salt of 3-oxoadipic acid are precipitated by cooling crystallization or insulated crystallization, followed by obtaining crystals of 3-oxoadipic acid and/or the salt of 3-oxoadipic acid by centrifugation, filtration, and/or the like; and a method in which alcohol is added to the culture to produce 3-oxoadipic acid ester, and then the 3-oxoadipic acid ester is recovered by a distillation operation, followed by performing hydrolysis to obtain 3-oxoadipic acid. Examples of the salt of 3-oxoadipic acid include Na salt, K salt, Ca salt, Mg salt, and ammonium salt.

EXAMPLES

The present invention is described below concretely by way of Examples. However, the present invention is not limited to these.

Reference Example 1 Providing 3-Oxoadipic Acid

For use in quantitative analysis of 3-oxoadipic acid produced by microorganisms, samples of the substance were provided by chemical synthesis.

First, 1.5 L of super-dehydrated tetrahydrofuran (manufactured by Wako Pure Chemical Industries, Ltd.) was added to 13.2 g (0.1 mol) of succinic acid monomethyl ester (manufactured by Wako Pure Chemical Industries, Ltd.), and 16.2 g (0.1 mol) of carbonyldiimidazole (manufactured by Wako Pure Chemical Industries, Ltd.) was added thereto with stirring, followed by stirring the resulting mixture under nitrogen atmosphere for 1 hour at room temperature. To this suspension, 15.6 g (0.1 mol) of malonic acid monomethyl ester potassium salt and 9.5 g (0.1 mol) of magnesium chloride were added. The resulting mixture was stirred under a nitrogen atmosphere for 1 hour at room temperature, and then stirred at 40° C. for 12 hours. After the reaction, 0.05 L of 1 mol/L hydrochloric acid was added to the mixture at room temperature, and extraction with ethyl acetate was carried out. By separation purification by silica gel column chromatography (hexane:ethyl acetate=1:5), 13.1 g of pure 3-oxohexanedicarboxylic acid dimethyl ester was obtained. Yield: 70%.

To 5 g (0.026 mol) of the 3-oxohexanedicarboxylic acid dimethyl ester obtained, 26 mL of methanol (manufactured by Kokusan Chemical Co., Ltd.) was added, and 12 mL of 5 mol/L aqueous sodium hydroxide solution was added to the resulting mixture with stirring, followed by stirring the mixture at room temperature overnight. After completion of the reaction, 12 mL of 5 mol/L hydrochloric acid was added to the reaction product, and extraction with 100 mL of ethyl acetate (manufactured by Wako Pure Chemical Industries, Ltd.) was carried out. After concentrating the resulting extract using a rotary evaporator, recrystallization with acetone/petroleum ether was carried out to obtain 2 g of pure 3-oxoadipic acid. Yield: 47%.

$^1$H-NMR Spectrum of 3-Oxoadipic Acid:
$^1$H-NMR (400 MHz, D$_2$O): δ 2.62 (t, 2H), δ 2.88 (t, 2H), δ 3.73 (s, 1H).

Example 1 3-Oxoadipic Acid Production Test Using Aliphatic Compound

[Microbial Culture]

The 3-oxoadipic acid productivities of the microorganisms shown in the following Table 1 (all microorganisms were purchased from microorganism-distributing agencies; the distributors are described in the strain names) were investigated. To 5 mL of a medium prepared such that it contains 10 g/L tryptone, 5 g/L yeast extract, 5 g/L sodium chloride, and, as inducers, 2.5 mM each of benzoic acid, cis,cis-muconic acid, terephthalic acid, protocatechuic acid, catechol, adipic acid, phenylalanine, and phenethylamine, wherein the pH was adjusted to 7, a loopful of each microorganism was inoculated. Shake culture was then carried out at 30° C. until the microorganism was sufficiently suspended (preculture). To the culture liquid, 10 mL of 0.9% sodium chloride was added, and the microbial cells were centrifuged, followed by completely removing the supernatant, thereby washing the microbial cells. After carrying out this operation three times, the microbial cells were suspended in 1 mL of 0.9% sodium chloride. To 5 mL of the medium having the following composition containing aliphatic compounds as carbon sources, 0.5 mL of the resulting suspension was added, and shake culture was performed at 30° C. for 20 hours (main culture). The main culture liquid was subjected to centrifugation to separate microbial cells, and the resulting supernatant was analyzed by LC-MS/MS.

Medium Composition for the Main Culture:
10 g/L succinic acid
10 g/L glucose
10 g/L glycerol
1 g/L ammonium sulfate
50 mM potassium phosphate
0.025 g/L magnesium sulfate
0.0625 mg/L iron sulfate
2.7 mg/L manganese sulfate 0.33 mg/L calcium chloride
1.25 g/L sodium chloride
2.5 g/L Bacto tryptone
1.25 g/L yeast extract
pH 6.5.

[Quantitative Analysis of 3-Oxoadipic Acid]

Quantitative analysis of 3-oxoadipic acid by LC-MS/MS was carried out under the following conditions.

HPLC: 1290 Infinity (manufactured by Agilent Technologies)
Column: Synergi hydro-RP (manufactured by Phenomenex); length, 100 mm; inner diameter, 3 mm; particle size, 2.5 μm
Mobile phase: 0.1% aqueous formic acid solution/methanol=70/30
Flow rate: 0.3 mL/minute
Column temperature: 40° C.
LC detector: DAD (210 nm)
MS/MS: Triple-Quad LC/MS (manufactured by Agilent Technologies)
Ionization method: ESI negative mode.

The concentration of 3-oxoadipic acid accumulated in the culture supernatant was as shown in Table 1. It was able to be confirmed that all microorganisms have a capacity to produce 3-oxoadipic acid.

TABLE 1

| Test microorganism | 3-Oxoadipic acid (mg/L) |
| --- | --- |
| Serratia plymuthica NBRC102599 | 350 |
| Serratia grimesii NBRC13537 | 250 |
| Serratia ficaria NBRC102596 | 230 |
| Corynebacterium glutamicum ATCC13826 | 190 |
| Corynebacterium glutamicum ATCC21492 | 180 |
| Corynebacterium glutamicum ATCC13032 | 116 |
| Corynebacterium acetoacidophilum ATCC 21270 | 45 |
| Pseudomonas putida NBRC3738 | 43 |
| Corynebacterium acetoglutamicum ATCC 15806 | 27 |
| Pseudomonas fragi NBRC3458 | 25 |
| Bacillus megaterium ATCC10778 | 22 |
| Corynebacterium ammoniagenes ATCC 6871 | 13 |
| Hafnia alvei NBRC3731 | 10 |
| Acinetobacter radioresistens NBRC102413 | 8.0 |
| Pseudomonas reptilivora ATCC14039 | 7.4 |
| Bacillus badius ATCC 14574 | 6.8 |
| Escherichia fergusonii NBRC102419 | 6.3 |
| Akaligenes faecalis NBRC13111 | 6.2 |
| Shimwellia blattae NBRC105725 | 5.8 |
| Pseudomonas fluorescens NBRC3925 | 5.0 |
| Planomicrobium okeanokoites NBRC12536 | 3.9 |
| Nocardioides albus NBRC13917 | 3.4 |
| Yarrowia lipolytica NBRC0717 | 3.1 |
| Escherichia coli NBRC12713 | 2.4 |
| Pseudomonas azotoformans NBRC12693 | 2.4 |
| Cupriavidus necator NBRC102504 | 2.1 |
| Rhodosporidium toruloides ATCC 10788 | 1.2 |
| Streptomyces olivaceus NBRC3049 | 1.0 |

Example 2 3-Oxoadipic Acid Production Test Using Single Aliphatic Compound

Each of *S. plymuthica* NBRC102599, *C. glutamicum* ATCC13826, and *P. fragi* NBRC3458 was cultured under the same conditions as in Example 1 except that 10 g/L of one of succinic acid, glucose, and glycerol was included as a sole carbon source in the main culture. Thereafter, quantitative analysis of 3-oxoadipic acid in the culture supernatant was carried out. The results for the three strains of microorganisms are shown in Tables 2 to 4, respectively.

TABLE 2

| Carbon source | 3-Oxoadipic acid (mg/L) |
| --- | --- |
| Succinic acid | 16 |
| Glucose | 16 |
| Glycerol | 11 |

TABLE 3

| Carbon source | 3-Oxoadipic acid (mg/L) |
| --- | --- |
| Succinic acid | 10 |
| Glucose | 10 |
| Glycerol | 5.3 |

TABLE 4

| Carbon source | 3-Oxoadipic acid (mg/L) |
| --- | --- |
| Succinic acid | 3.2 |
| Glucose | 2.6 |
| Glycerol | 1.1 |

Reference Example 2 Growth Test Using Single Aliphatic Compound

A loopful of each of *S. plymuthica* NBRC102599, *C. glutamicum* ATCC13826, and *P. fragi* NBRC3458 was inoculated to a growth test medium containing 10 g/L of one of the aliphatic compounds shown in Tables 5 to 7 as a sole carbon source in the culture, and shake culture was carried out at 30° C. Two days after the beginning of the culture, the turbidity (McFarland units) of the culture liquid was measured using a densitometer DEN-1B (Wakenbtech Co., Ltd.). At the same time, culture was carried out to provide a control without addition of a carbon source. The difference, from the control, in the turbidity was calculated. The results for the three strains of microorganisms are shown in Tables 5 to 7, respectively.

Growth Test Medium Composition (*S. plymuthica* and *P. fragi*):
10 g/L carbon source
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
pH 6.5.

Growth Test Medium Composition (*C. glutamicum*):
10 g/L carbon source
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
0.03 mg/L biotin
1 mg/L thiamine hydrochloride
1 mg/L protocatechuic acid
pH 6.5.

TABLE 5

| Carbon source | McFarland units (Difference from control) |
| --- | --- |
| Succinic acid | >6 |
| Glucose | 5.8 |
| Xylose | >6 |
| Glycerol | 1.9 |
| Acetic acid | 0.9 |
| Galactitol | −0.5 |
| Ethylene glycol | −0.3 |
| D(−)-Tartaric acid | −0.2 |

TABLE 6

| Carbon source | McFarland units (Difference from control) |
| --- | --- |
| Succinic acid | 4.7 |
| Glucose | 5.4 |
| Xylose | 0.0 |
| Glycerol | 3.7 |
| Acetic acid | 5.9 |
| Galactitol | −0.4 |
| Ethylene glycol | −0.4 |
| D(−)-Tartaric acid | −0.4 |

TABLE 7

| Carbon source | McFarland units (Difference from control) |
| --- | --- |
| Succinic acid | 3.0 |
| Glucose | 1.2 |
| Xylose | 1.0 |
| Glycerol | 0.9 |
| Acetic acid | 1.1 |
| Galactitol | 0.0 |
| Ethylene glycol | −0.2 |
| D(−)-Tartaric acid | −0.3 |

Example 3 3-Oxoadipic Acid Production Test Using Two Kinds of Aliphatic Compounds Each of *S. plymuthica* NBRC102599, *C. glutamicum* ATCC13826, and *P. fragi* NBRC3458 was cultured under the same conditions as in Example 1 except that 10 g/L each of two kinds of aliphatic compounds shown in Tables 8 to 10 were contained as carbon sources in the main culture. Thereafter, quantitative analysis of 3-oxoadipic acid in the culture supernatant was carried out. At the same time, culture was carried out to provide a control using only succinic acid as a carbon source. The difference, from the control, in the concentration of 3-oxoadipic acid accumulated was calculated. The results for the three strains of microorganisms are shown in Tables 8 to 10, respectively.

TABLE 8

| Carbon source | | 3-Oxoadipic acid (mg/L) (Difference from control) |
| --- | --- | --- |
| Glucose | Glycerol | 5.0 |
| Succinic acid | Glucose | 150 |
| Succinic acid | Xylose | 120 |
| Succinic acid | Glycerol | 79 |
| Succinic acid | Acetic acid | 13 |
| Succinic acid | Galactitol | −4.6 |

TABLE 8-continued

| Carbon source | | 3-Oxoadipic acid (mg/L) (Difference from control) |
| --- | --- | --- |
| Succinic acid | Ethylene glycol | −5.2 |
| Succinic acid | D(−)-Tartaric acid | −4.5 |

TABLE 9

| Carbon source | | 3-Oxoadipic acid (mg/L) (Difference from control) |
| --- | --- | --- |
| Glucose | Glycerol | 2.3 |
| Succinic acid | Glucose | 180 |
| Succinic acid | Xylose | −1.2 |
| Succinic acid | Glycerol | 26 |
| Succinic acid | Acetic acid | 13 |
| Succinic acid | Galactitol | −1.2 |
| Succinic acid | Ethylene glycol | −1.2 |
| Succinic acid | D(−)-Tartaric acid | −1.2 |

TABLE 10

| Carbon source | | 3-Oxoadipic acid (mg/L) (Difference from control) |
| --- | --- | --- |
| Glucose | Glycerol | 1.5 |
| Succinic acid | Glucose | 33 |
| Succinic acid | Xylose | 17 |
| Succinic acid | Glycerol | 11 |
| Succinic acid | Acetic acid | 6.1 |
| Succinic acid | Galactitol | 0.0 |
| Succinic acid | Ethylene glycol | −0.7 |
| Succinic acid | D(−)-Tartaric acid | −0.1 |

Example 4 3-Oxoadipic Acid Production Test Using Single Inducer

Each of *S. plymuthica* NBRC102599, *C. glutamicum* ATCC13826, and *P. fragi* NBRC3458 was precultured using media containing 2.5 mM of a compound shown in Tables 11 to 13 as an inducer, or a medium containing no inducer. Culture was performed under the same conditions as in Example 1 except that a medium containing 10 g/L each of succinic acid and glucose as carbon sources was used in the main culture. Thereafter, quantitative analysis of 3-oxoadipic acid in the culture supernatant was carried out. The results for the three strains of microorganisms are shown in Tables 11 to 13, respectively.

TABLE 11

| Inducer | 3-Oxoadipic acid (mg/L) |
| --- | --- |
| No addition | 16 |
| Benzoic acid | 53 |
| Catechol | 35 |
| Protocatechuic acid | 90 |
| Adipic acid | 55 |

TABLE 12

| Inducer | 3-Oxoadipic acid (mg/L) |
| --- | --- |
| No addition | 49 |
| Benzoic acid | 120 |
| Catechol | 110 |
| Protocatechuic acid | 52 |
| Adipic acid | 82 |

TABLE 13

| Inducer | 3-Oxoadipic acid (mg/L) |
| --- | --- |
| No addition | 9.2 |
| Benzoic acid | 9.6 |
| Catechol | 15 |
| Protocatechuic acid | 15 |
| Adipic acid | 20 |

Example 5 Production Example of 3-Oxoadipic Acid

To 5 mL of LB medium, a loopful of *Serratia plymuthica* NBRC102599, which was able to be confirmed to be a microorganism having a capacity to produce 3-oxoadipic acid in Example 1, was inoculated, and shake culture was carried out at 30° C. until the microorganism was sufficiently suspended (pre-preculture). To 100 mL of a medium containing 10 g/L tryptone, 5 g/L yeast extract, 5 g/L sodium chloride, 2.5 mM benzoic acid, 2.5 mM catechol, 2.5 mM cis,cis-muconic acid, 2.5 mM terephthalic acid, 2.5 mM protocatechuic acid, 2.5 mM adipic acid, 2.5 mM phenylalanine, and 2.5 mM phenethylamine, at pH 7, 2 mL of the pre-preculture liquid was added, and shake culture was carried out at 30° C. until the microorganism was sufficiently suspended (preculture). The preculture liquid was subjected to three times of washing with 200 mL of 0.9% sodium chloride in the same manner as in Example 1, and the microbial cells were suspended in 10 mL of 0.9% sodium chloride. To 100 mL of the same main culture medium as in Example 1, 10 mL of the resulting suspension was added, and shake culture was performed at 30° C. for 20 hours (main culture). The main culture liquid was centrifuged to separate microbial cells, and the resulting supernatant was analyzed by LC-MS/MS in the same manner as in Example 1. As a result, the concentration of 3-oxoadipic acid accumulated in the culture supernatant was found to be 260 mg/L.

Subsequently, the supernatant from the main culture was concentrated under reduced pressure, to obtain 12 mL of a concentrate having a 3-oxoadipic acid concentration of 2200 mg/L. The concentrate was injected into HPLC to which a fraction collection device was connected, and a fraction having the same elution time as a 3-oxoadipic acid sample was collected. This operation was carried out ten times for removal of impurities in the culture liquid, to obtain an aqueous 3-oxoadipic acid solution. The preparative HPLC used for the collection of 3-oxoadipic acid was carried out under the following conditions.
HPLC: SHIMADZU 20A (manufactured by Shimadzu Corporation)
Column: Synergi hydro-RP (manufactured by Phenomenex); length, 250 mm; inner diameter, 10 mm; particle size, 4
Mobile phase: 5 mM aqueous formic acid solution/acetonitrile=98/2
Flow rate: 4 mL/minute
Injection volume: 1 mL
Column temperature: 45° C.
Detector: UV-VIS (210 nm)
Fraction collection device: FC204 (manufactured by Gilson)

Subsequently, the aqueous 3-oxoadipic acid solution was concentrated under reduced pressure, to obtain 22 mg of crystals. As a result of analysis of the crystals by $^1$H-NMR, it was able to confirm that the obtained crystals were 3-oxoadipic acid.

Comparative Example 1 Microorganism Having No Capacity to Produce 3-Oxoadipic Acid In order to investigate the 3-oxoadipic acid productivity of the microorganism shown in Table 14, microbial culture was carried out under the same conditions as in Example 1, and quantitative analysis of 3-oxoadipic acid was carried out. As a result, no 3-oxoadipic acid was detected in the culture supernatant.

TABLE 14

| Microbial strain | 3-Oxoadipic acid (mg/L) |
| --- | --- |
| *Zymomonas mobilis* NBRC13756 | N.D. |

Comparative Example 2 Culture without Addition of Carbon Source

The microorganisms shown in Table 1 were cultured under the same conditions as in Example 1 except that a medium having a composition containing no aliphatic compound (succinic acid, glucose, or glycerol) as a carbon source was used. As a result of quantitative analysis of 3-oxoadipic acid, no 3-oxoadipic acid was detected in the culture supernatant. From this result, it was confirmed that the 3-oxoadipic acid that was able to be quantified in Example 1 was a product resulted by metabolism of aliphatic compounds by the microorganisms.

Example 6 3-Oxoadipic Acid Production Test Using Various Microorganisms

The microorganisms shown in Table 15 (all microorganisms were purchased from microorganism-distributing agencies; the distributors are described in the strain names) were subjected to preculture and microbial cell washing under the same conditions as in Example 1 except that each of ferulic acid, p-coumaric acid, benzoic acid, cis,cis-muconic acid, protocatechuic acid, and catechol was added to 2.5 mM as an inducer to the preculture medium. To 5 mL of the medium having the composition shown below, 0.5 mL of the suspension after the washing was added, and shake culture was performed at 30° C. for 48 hours.
10 g/L succinic acid
10 g/L glucose
10 g/L glycerol
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
2.5 g/L Bacto tryptone
1.25 g/L yeast extract
pH 6.5.

The results of quantitative analysis of 3-oxoadipic acid accumulated in the culture supernatant are shown in Table 15. From these results, it was confirmed that all microorganisms have a capacity to produce 3-oxoadipic acid.

TABLE 15

| Test microorganism | 3-Oxoadipic acid (mg/L) |
|---|---|
| Serratia entomophila DSM12358 | 24 |
| Serratia nematodiphila DSM21420 | 6.2 |
| Serratia fonticola DSM9663 | 6.1 |
| Serratia fonticola NBRC102597 | 6.1 |
| Serratia odorifera NBRC102598 | 2.0 |
| Corynebacterium glutamicum ATCC 14020 | 58 |
| Corynebacterium glutamicum ATCC13059 | 131 |
| Corynebacterium glutamicum ATCC13060 | 137 |
| Corynebacterium glutamicum ATCC13287 | 63 |
| Corynebacterium glutamicum ATCC14067 | 26 |
| Corynebacterium glutamicum ATCC21086 | 51 |
| Corynebacterium glutamicum ATCC21127 | 32 |
| Corynebacterium glutamicum ATCC21128 | 42 |
| Corynebacterium glutamicum ATCC21129 | 36 |
| Corynebacterium glutamicum ATCC21300 | 34 |
| Corynebacterium glutamicum ATCC21474 | 55 |
| Corynebacterium glutamicum ATCC21526 | 57 |
| Corynebacterium glutamicum ATCC21527 | 57 |
| Corynebacterium glutamicum ATCC21650 | 117 |
| Corynebacterium glutamicum ATCC21651 | 60 |
| Corynebacterium ammoniagenes NBRC12071 | 22 |
| Corynebacterium ammoniagenes NBRC12072 | 14 |
| Microbacterium ammoniaphilum ATCC15354 | 42 |
| Bacillus megaterium ATCC10778 | 22 |
| Pseudomonas putida ATCC8209 | 7.2 |
| Pseudomonas putida NBRC12653 | 6.2 |
| Pseudomonas putida NBRC12996 | 3.4 |
| Pseudomonas sp. NBRC12691 | 3.0 |
| Pseudomonas putida ATCC12633 | 3.0 |
| Pseudomonas putida ATCC17642 | 2.5 |
| Pseudomonas sp. ATCC13867 | 1.9 |
| Pseudomonas sp. ATCC14718 | 1.3 |
| Hafnia alvei ATCC 9760 | 7.0 |
| Cupriavidus necator DSM545 | 1.6 |
| Saccharomyces cerevisiae NBRC0206 | 1.6 |
| Yersinia ruckeri NBRC102019 | 1.4 |

Example 7 3-Oxoadipic Acid Production Test without Addition of Inducers

The microorganisms shown in Table 16 were subjected to preculture and microbial cell washing under the same conditions as in Example 6 except that the inducers used in Example 6 were not added. To 5 mL of the medium having the composition shown below, 0.5 mL of the suspension after the washing was added, and shake culture was performed at 30° C. for 48 hours.

10 g/L succinic acid
10 g/L glucose
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
2.5 g/L Bacto tryptone
1.25 g/L yeast extract
pH 6.5.

The results of quantitative analysis of 3-oxoadipic acid in the culture supernatant are shown in Table 16.

From these results, it was confirmed that the microorganisms shown in Table 16 have a capacity to produce 3-oxoadipic acid even in cases where preculture is carried out without addition of inducers.

TABLE 16

| Test microorganism | 3-Oxoadipic acid production (mg/L) |
|---|---|
| Serratia grimesii NBRC13537 | 2.5 |
| Serratia ficaria NBRC102596 | 3.2 |
| Serratia plymuthica NBRC102599 | 12.4 |
| Serratia fonticola NBRC102597 | 2.0 |
| Serratia odorifera NBRC102598 | 1.6 |
| Serratia entomophila DSM12358 | 3.2 |
| Serratia nematodiphila DSM21420 | 1.0 |
| Corynebacterium glutamicum ATCC13032 | 14.6 |
| Corynebacterium glutamicum ATCC21492 | 5.7 |
| Corynebacterium glutamicum ATCC13826 | 9.1 |

Example 8 3-Oxoadipic Acid Production Test Using p-Coumaric Acid or Ferulic Acid as Inducer The microorganisms shown in Table 17 were subjected to preculture and microbial cell washing under the same conditions as in Example 6 except that p-coumaric acid or ferulic acid, among the substances added as inducers to the preculture medium in Example 6, was added to 0.5 mM. To 5 mL of the medium having the composition shown in Example 7, 0.5 mL of the suspension after the washing was added, and shake culture was performed at 30° C. for 48 hours. The results of quantitative analysis of 3-oxoadipic acid in the culture supernatant are shown in Table 17. From these results, it was found that the productivity of 3-oxoadipic acid can be increased even by addition of p-coumaric acid or ferulic acid alone as an inducer to the preculture medium compared to cases where neither of these is added.

TABLE 17

| | 3-Oxoadipic acid production (mg/L) | | |
|---|---|---|---|
| Test microorganism | No addition | p-Coumaric acid added | Ferulic acid added |
| Serratia plymuthica NBRC102599 | 12.4 | 18.0 | 16.6 |
| Serratia grimesii NBRC13537 | 2.5 | 6.0 | 5.7 |
| Serratia ficaria NBRC102596 | 3.2 | 5.0 | 4.8 |
| Corynebacterium glutamicum ATCC13826 | 9.1 | 15.6 | 13.2 |
| Corynebacterium glutamicum ATCC21492 | 5.7 | 14.0 | 9.6 |
| Corynebacterium glutamicum ATCC13032 | 14.6 | 32.2 | 28.7 |
| Corynebacterium acetoglutamicum ATCC 15806 | 12.5 | 44.5 | 36.0 |
| Bacillus badius ATCC 14574 | 6.3 | 33.6 | 9.8 |
| Cupriavidus necator DSM545 | 1.4 | 3.4 | 3.2 |

Example 9 3-Oxoadipic Acid Production Test Using Ferulic Acid as Inducer at Various Concentrations The microorganisms shown in Table 18 were subjected to preculture in which, among the substances added as inducers to the preculture medium in Example 6, ferulic acid was added to the preculture medium in Example 7 to the concentrations shown in Table 18. Main culture was carried out under the same conditions as in Example 7, and quantitative analysis of 3-oxoadipic acid in the culture supernatant was carried out. The results are shown in Table 18. From these results, it was found that the productivity of 3-oxoadipic acid can be increased even by addition of ferulic acid alone as an inducer to the preculture medium.

TABLE 18

| Test microorganism | 3-Oxoadipic acid production (mg/L) Concentration of ferulic acid added (mM) | | | | | | |
|---|---|---|---|---|---|---|---|
| | 0.00 | 0.05 | 0.10 | 0.25 | 0.50 | 1.00 | 2.50 |
| S. grimesii NBRC13537 | 1.4 | 1.5 | 1.5 | 1.6 | 1.8 | 1.8 | 2.5 |
| S. ficaria NBRC102596 | 2.2 | 2.5 | 2.5 | 2.8 | 2.9 | 3.1 | 3.4 |
| S. plymuthica NBRC102599 | 17.1 | 17.7 | 17.8 | 17.8 | 18.6 | 20.5 | 24.7 |

Example 10 3-Oxoadipic Acid Production Test Using p-Coumaric Acid as Inducer at Various Concentrations The microorganism shown in Table 19 was subjected to preculture in which, among the substances added as inducers to the preculture medium in Example 6, p-coumaric acid was added to the preculture medium in Example 7 to the concentrations shown in Table 19. Main culture was carried out under the same conditions as in Example 7, and quantitative analysis of 3-oxoadipic acid in the culture supernatant was carried out. The results are shown in Table 19. From these results, it was found that the productivity of 3-oxoadipic acid can be increased even by addition ofp-coumaric acid alone as an inducer to the preculture medium.

TABLE 19

| Test microorganism | 3-Oxoadipic acid production (mg/L) Concentration of p-coumaric acid added (mM) | | | | | | |
|---|---|---|---|---|---|---|---|
| | 0.00 | 0.05 | 0.10 | 0.25 | 0.50 | 1.00 | 2.50 |
| S. grimesii NBRC13537 | 1.4 | 1.7 | 1.8 | 2.0 | 2.3 | 3.0 | 6.5 |

Reference Example 3 Method of Preparing Filamentous Fungus-Derived Cellulase (Culture Liquid)

A filamentous fungus-derived cellulase (culture liquid) was prepared by the following method.

[Preculture]

The mixture of 5% (w/vol) corn steep liquor (CSL), 2% (w/vol) glucose, 0.37% (w/vol) ammonium tartrate, 0.14 (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid, and 0.0026% (w/vol) hexaammonium heptamolybdate tetrahydrate in distilled water was prepared, and 100 mL of this mixture was placed in a baffled 500-mL Erlenmeyer flask, followed by sterilization by autoclaving at a temperature of 121° C. for 15 minutes. After allowing the mixture to cool, PE-M and Tween 80, each of which was sterilized by autoclaving at a temperature of 121° C. for 15 minutes separately from the mixture, were added thereto to 0.01% (w/vol) each. To this preculture medium, Trichoderma reesei ATCC66589 was inoculated at 1×10⁵ cells/mL, and the cells were cultured at a temperature of 28° C. for 72 hours with shaking at 180 rpm to perform preculture (shaker: BIO-SHAKER BR-40LF, manufactured by TAITEC CORPORATION).

[Main Culture]

The mixture of 5% (w/vol) corn steep liquor (CSL), 2% (w/vol) glucose, 10% (w/vol) cellulose (manufactured by Asahi Kasei Chemicals Corporation; trade name, Avicel), 0.37% (w/vol) ammonium tartrate, 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid, and 0.0026% (w/vol) hexaammonium heptamolybdate tetrahydrate in distilled water was prepared, and 2.5 L of this mixture was placed in a 5-L stirring jar (manufactured by ABLE, DPC-2A), followed by sterilization by autoclaving at a temperature of 121° C. for 15 minutes. After allowing the mixture to cool, PE-M and Tween 80, each of which was sterilized by autoclaving at a temperature of 121° C. for 15 minutes separately from the mixture, were added thereto to 0.1% each. To the resulting mixture, 250 mL of the preculture of Trichoderma reesei ATCC66589 preliminarily prepared with a liquid medium by the method described above was inoculated. Shake culture was then carried out at a temperature of 28° C. for 87 hours at 300 rpm at an aeration rate of 1 vvm. After centrifugation, the supernatant was subjected to membrane filtration ("Stericup-GV", manufactured by Millipore, material: PVDF). The culture liquid prepared under the above conditions was used as a filamentous fungus-derived cellulase in the following Reference Examples.

Reference Example 4 Measurement of Cellulase Concentration

The cellulase concentration in the aqueous solution was evaluated using as a standard the value of the protein concentration (mg/mL) in an enzyme liquid as measured by the Bradford method. The protein concentration was measured using an assay kit based on the Bradford method (Quick Start Bradford Protein Assay, manufactured by Bio-Rad).

Reference Example 5 Preparation of Cellulose-Containing-Biomass-Derived Saccharified Liquid To bagasse with a dry weight of 1 kg, 30 g of caustic soda was added at a biomass feeding amount of 5%. The resulting mixture was reacted at 90° C. for 3 hours to prepare alkali-treated bagasse. The alkali-treated bagasse was subjected to solid-liquid separation by screw pressing to obtain a solid-liquid-separated solid having a moisture content of 60%.

The solid-liquid-separated solid was resuspended at a solid concentration of 5%, and hydrolysis was carried out with the filamentous fungus-derived cellulase prepared in Reference Example 3 at a protein amount of 8 mg/g-bagasse according to the measurement described in Reference Example 4, to obtain a saccharified liquid. The hydrolysis was carried out at 40° C. at pH 7.0 for a reaction time 24 hours. The solid component was removed from the obtained saccharified liquid using a screw decanter, and the whole amount of the recovered saccharified liquid was filtered through a microfiltration membrane having a pore size of 0.22 μm, followed by subjecting the obtained permeate to filtration treatment through an ultrafiltration membrane. As the ultrafiltration membrane, TMUS10k (manufactured by Toray Membrane USA; material: polyvinylidene fluoride; molecular weight cutoff: 10,000) was used. In the ultrafiltration, filtration treatment was carried out using a flat membrane filtration unit "SEPA-II" (GE Osmonics) at a membrane surface linear velocity of 20 cm/sec. and a filtration pressure of 3 MPa until the volume of the liquid collected from the feed side reached 0.6 L, to obtain a saccharified liquid in the permeate side.

Filtration treatment of the obtained saccharified liquid was carried out using a separation membrane (manufactured by Synder; NFW (material: piperazine polyamide; molecular weight cutoff, 300 to 500)). The filtration treatment was carried out at a membrane surface linear velocity of 20 cm/sec. and a filtration pressure of 3 MPa until the concentration rate in the feed side reached 12-fold, to obtain a saccharified liquid in the permeate side.

The obtained saccharified liquid was concentrated using an evaporator to prepare a saccharified liquid containing 100 g/L glucose, 22.3 g/L xylose, 0.5 g/L coumaric acid, and 0.06 g/L ferulic acid. The final pH of the saccharified liquid was adjusted to 7 using 6 N sodium hydroxide.

Example 11 3-Oxoadipic Acid Production Test Using Cellulose-Containing-Biomass-Derived Saccharified Liquid For the microorganisms shown in Table 20, a 3-oxoadipic acid production test was carried out using as a carbon source the cellulose-containing-biomass-derived saccharified liquid prepared in Reference Example 5.

In 5 mL of a preculture medium prepared to have the following composition using the cellulose-containing-biomass-derived saccharified liquid, each microorganism was cultured with shaking at 30° C. until the microorganism was sufficiently suspended (preculture). Subsequently, the microbial cells were washed under the same conditions as in Example 6. To 5 mL of a main culture medium prepared to have the following composition using the cellulose-containing-biomass-derived saccharified liquid, 0.5 mL of the suspension after the washing was added, and culture was performed with shaking at 30° C. for 48 hours. For comparison, culture was performed under the same conditions as described above except that carbon sources containing neither p-coumaric acid nor ferulic acid were used for the preculture and the main culture. The results of quantitative analysis of 3-oxoadipic acid in the culture supernatant are shown in Table 20. From these results, it was found that the productivity of 3-oxoadipic acid can be increased also in cases where culture is carried out using a cellulose-containing-biomass-derived saccharified liquid containing p-coumaric acid and ferulic acid, relative to cases where carbon sources containing neither p-coumaric acid nor ferulic acid are used.

Medium Composition for the Preculture:
5 g/L glucose
1.1 g/L xylose
25 mg/L p-coumaric acid
3 mg/L ferulic acid
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
2.5 g/L Bacto tryptone
1.25 g/L yeast extract
pH 6.5.

Medium Composition for the Main Culture:
50 g/L glucose
11 g/L xylose
250 mg/L p-coumaric acid
30 mg/L ferulic acid
10 g/L succinic acid
1 g/L ammonium sulfate
50 mM potassium phosphate
0.025 g/L magnesium sulfate
0.0625 mg/L iron sulfate
2.7 mg/L manganese sulfate
0.33 mg/L calcium chloride
1.25 g/L sodium chloride
2.5 g/L Bacto tryptone
1.25 g/L yeast extract
pH 6.5.

TABLE 20

| | 3-Oxoadipic acid production (mg/L) | |
|---|---|---|
| Test microorganism | Reagent saccharides | Sugar liquid |
| Serratia plymuthica NBRC102599 | 8.0 | 11.3 |
| Serratia grimesii NBRC13537 | 1.3 | 5.1 |
| Serratia ficaria NBRC102596 | 3.5 | 5.3 |
| Corynebacterium glutamicum ATCC13826 | 14.1 | 28.3 |
| Corynebacterium glutamicum ATCC21492 | 9.8 | 24.1 |
| Corynebacterium glutamicum ATCC13032 | 18.7 | 26.4 |

Example 12 3-Oxoadipic Acid Production Test Using Two Kinds of Carbon Sources

The microorganisms shown in Table 21 and Table 22 were precultured using the same medium as in Example 6, and then cultured in media containing 10 g/L each of the compounds shown in Table 21 and Table 22 as carbon sources under the same conditions as in Example 6. Thereafter, quantitative analysis of 3-oxoadipic acid in the culture supernatant was carried out. The results are shown in Table 21 and Table 22. From these results, it was found that 3-oxoadipic acid can be efficiently produced also by culture using two kinds of carbon sources.

TABLE 21

| | 3-Oxoadipic acid production (mg/L) (with addition of inducers) Carbon source | | | | | | | |
|---|---|---|---|---|---|---|---|---|
| Test microorganism | Glucose Glycerol | Glucose Succinic acid | Glycerol Succinic acid | Xylose Succinic acid | Arabinose Succinic acid | Glucose 2-Oxoglutaric acid | Glycerol 2-Oxoglutaric acid | Xylose 2-Oxoglutaric acid | Arabinose 2-Oxoglutaric acid |
| *S. grimesii* NBRC13537 | 17.5 | 136.9 | 185.3 | 113.2 | 169.4 | 40.5 | 115.0 | 151.3 | 123.0 |
| *S. ficaria* NBRC102596 | 15.3 | 68.6 | 42.6 | 19.0 | 84.1 | 45.1 | 75.1 | 73.7 | 61.0 |
| *S. plymuthica* NBRC102599 | 26.3 | 182.3 | 84.8 | 64.7 | 172.4 | 35.1 | 94.1 | 103.4 | 69.5 |

TABLE 22

| | 3-Oxoadipic acid production (mg/L) (with addition of inducers) Carbon source | | |
|---|---|---|---|
| Test microorganism | Glucose Glycerol | Glucose Succinic acid | Glycerol Succinic acid |
| *C. glutamicum* ATCC13032 | 16.3 | 115.5 | 16.4 |
| *C. glutamicum* ATCC21492 | 13.4 | 250.3 | 14.2 |
| *C. glutamicum* ATCC13826 | 13.7 | 188.8 | 16.3 |

Example 13 3-Oxoadipic Acid Production Test Using Two Kinds of Carbon Sources at Various Concentrations The microorganisms shown in Table 23 and Table 24 were precultured using the same medium as in Example 6, and then cultured in media containing as carbon sources the compounds shown in Table 23 and Table 24 at the concentrations shown in the Tables, under the same conditions as in Example 6 for 48 to 120 hours. Thereafter, quantitative analysis of 3-oxoadipic acid in the culture supernatant was carried out. The results are shown in Table 23 and Table 24. From these results, it was found that 3-oxoadipic acid can be produced also in cases where the ratios of carbon sources are changed.

TABLE 23

| | 3-Oxoadipic acid production (mg/L) (with addition of inducers) Carbon source | | | | | | |
|---|---|---|---|---|---|---|---|
| Test microorganism | Glucose 25 g/L Succinic acid 10 g/L | Glucose 50 g/L Succinic acid 10 g/L | Xylose 25 g/L Succinic acid 10 g/L | Xylose 50 g/L Succinic acid 10 g/L | Glucose 10 g/L Succinic acid 20 g/L | Glucose 100 g/L Succinic acid 20 g/L | Xylose 50 g/L Succinic acid 20 g/L |
| *S. grimesii* NBRC13537 | 114.8 | 120.9 | 90.8 | 123.2 | 242.7 | 241.5 | 382.9 |
| *S. ficaria* NBRC102596 | 13.5 | 18.1 | 35.3 | 37.4 | 65.9 | 165.4 | 103.6 |
| *S. plymuthica* NBRC102599 | 81.6 | 71.9 | 197.6 | 213.6 | 268.2 | 222.9 | 247.3 |

Example 14 3-Oxoadipic Acid Production Test Using Single Carbon Source

The microorganisms shown in Table 24 and Table 25 were precultured without addition of an inducer using the same medium as in Example 7, and then cultured in media containing 10 g/L of one of succinic acid, glucose, and glycerol as a carbon source, under the same conditions as in Example 7. Thereafter, quantitative analysis of 3-oxoadipic acid in the culture supernatant was carried out. The results are shown in Table 24. The same experiment was carried out under the same conditions as in Example 6, wherein inducers were added only to the preculture medium. The amounts of 3-oxoadipic acid produced are shown in Table 25. From these results, it was found that 3-oxoadipic acid can be produced even in cases where a sole carbon source is used, and that the amount of 3-oxoadipic acid produced can be increased by adding inducers to the preculture medium even in cases where a sole carbon source is used.

TABLE 24

| Test microorganism | 3-Oxoadipic acid production (mg/L) (without addition of Inducers) Carbon source | | | | |
|---|---|---|---|---|---|
| | Succinic acid | Glucose | Glycerol | Xylose | Arabinose |
| S. grimesii NBRC13537 | 1.2 | 1.0 | 1.5 | 1.8 | 1.7 |
| S. ficaria NBRC102596 | 1.0 | 1.3 | 3.0 | 2.0 | 1.5 |
| S. plymuthica NBRC102599 | 2.0 | 2.0 | 4.7 | 4.0 | 3.3 |

TABLE 25

| Test microorganism | 3-Oxoadipic acid production (mg/L) (with addition of inducers) Carbon source | | | | |
|---|---|---|---|---|---|
| | Succinic acid | Glucose | Glycerol | Xylose | Arabinose |
| S. grimesii NBRC13537 | 4.7 | 8.3 | 54.9 | 14.3 | 13.8 |
| S. ficaria NBRC102596 | 2.1 | 3.2 | 20.3 | 14.8 | 12.0 |
| S. plymuthica NBRC102599 | 15.8 | 16.3 | 10.6 | 11.1 | 10.9 |

INDUSTRIAL APPLICABILITY

By the present invention, 3-oxoadipic acid can be produced using a microorganism. The obtained 3-oxoadipic acid can be used as a raw material for polymers.

The invention claimed is:

1. A method of producing 3-oxoadipic acid, said method comprising the step of culturing at least one type of microorganism having a capacity to metabolize an aliphatic compound to produce 3-oxoadipic acid in a medium, said microorganism is selected from the group consisting of *Serratia plymuthica, Serratia grimesii, Serratia ficaria, Serratia fonticola, Serratia odorifera, Serratia entomophila*, and *Serratia nematodiphila*;

wherein said medium for culturing said microorganism contains an aliphatic compound utilizable as a sole carbon source for growth of the microorganism.

2. The method according to claim 1, wherein said microorganism is *Serratia plymuthica, Serratia grimesii*, or *Serratia ficaria*.

3. The method according to claim 1, wherein the medium for culturing said microorganism contains at least one carbon source selected from the group consisting of saccharides, succinic acid, 2-oxoglutaric acid, and glycerol.

4. The method according to claim 1, wherein said microorganism is cultured in a medium containing at least one inducer selected from the group consisting of ferulic acid and p-coumaric acid.

* * * * *